United States Patent [19]

Rogers et al.

[11] Patent Number: 5,126,323

[45] Date of Patent: Jun. 30, 1992

[54] HOMOGENEOUS PURIFIED K-FGF AND COMPOSITIONS CONTAINING THE SAME

[75] Inventors: David T. Rogers, Cochituate; Neil M. Wolfman, Dover; Jasbir S. Seehra, Tewskbury, all of Mass.

[73] Assignee: Genetics Institute, Inc., Cambridge, Mass.

[21] Appl. No.: 438,278

[22] Filed: Nov. 16, 1989

[51] Int. Cl.$^5$ .................. C07K 3/28; A61K 37/24
[52] U.S. Cl. ........................ 514/12; 514/21; 530/399; 530/324; 530/344; 530/345
[58] Field of Search ............. 530/399, 324, 344, 345; 514/12, 21

[56] References Cited

U.S. PATENT DOCUMENTS 4,785,079  11/1988  Gospodarowicz et al. ........ 530/399

FOREIGN PATENT DOCUMENTS

| 0237966 | 9/1987 | European Pat. Off. |
| 0259953 | 3/1988 | European Pat. Off. |
| 0275204 | 7/1988 | European Pat. Off. |
| 0326075 | 8/1989 | European Pat. Off. |
| WO86/07595 | 12/1986 | PCT Int'l Appl. |
| WO87/01728 | 3/1987 | PCT Int'l Appl. |

OTHER PUBLICATIONS

Patt, et al., *Kidney International* 23:603–610 (1983).
ten Dijke, *Biotechnology* 7:793–97 (Aug. 1989).
Thomas, *FASEB*:434–40 (1987).
Gospodarowicz, et al., *J. Cell Phys. Supp* 5:15–26 (1987).
Zhan, et al., *Mol and Cell Biol* 8(8):3487–95 (1988).
Marics, et al., *Oncogene* 4:335–40 (1989).
Dickson, et al., *Nature* 326:833 (1987).
Finch, et al., *Science* 245:752–55 (1989).
Iwane, et al., *Biochem. and Biophys. Res. Comm.* 146:470–77 (1987).
Fox, et al., *J. Biol Chem* 263(34):18452–58 (1988).
McGee, et al., *J. Surgical Research* 45:145–53 (1988).
Squires, et al., *J. Biol. Chem.* 263:16297–302 (1988).
Delli Bovi, et al., *PNAS USA* 84:5660–64 (1987).
Delli Bovi, et al., *Cell* 50:729–37 (1987).
Yoshida, et al., *PNAS USA* 84:7305–09 (1987).
Tiara, et al. *PNAS USA* 84:2980–84 (1987).
Delli Bovi, et al., *Mol and Cell Biol* 8(7):2933–41 (1988).

*Primary Examiner*—F. T. Moezie
*Attorney, Agent, or Firm*—Bruce M. Eisen; Patricia A. McDaniels; Luann Cserr

[57] ABSTRACT

Homogeneous K-FGF and a process for its production are provided. Also provided are pharmaceutical compositions for use in treating soft tissue injuries and musculo-skeletal disorders in mammals and methods of treatment. The purification of the bacterially produced K-FGF comprises reduction of a salt solution containing K-FGF to effect the precipitation of the product.

8 Claims, 2 Drawing Sheets

HOMOGENEOUS PURIFIED K-FGF AND COMPOSITIONS CONTAINING THE SAME

BACKGROUND

Growth factors mediate the processes by which a multicellular organism repairs various forms of damage to its integrity. Included in these processes are wound repair, for example skin closure after cuts or punctures, and compensatory growth, for example regrowth of function of certain organs to restore the original level of function and size after damage caused by mechanical or chemical means. The factors are necessary to the growth and differentiation of the cells that replace the destroyed or damaged tissue. Numerous active factors have been identified, based on the ability of tissue extracts containing the factors to stimulate the proliferation and differentiation of certain cultured cell lines.

Fibroblast growth factors (FGFs) appear to be specifically involved in mediating wound repair processes. They are angiogenic, hormone-like proteins that, among other things, stimulate the proliferation and induce or delay the differentiation of endothelial cells, which form the organism's blood vessels. See Patt et al., *Kidney International* 23:603-610 (1983). For a review of the role of growth factors generally in wound healing see ten Dijke, *Biotechnology* 7:793-97(Aug. 1989).

Two members of the FGF family, acidic and basic FGF (aFGF and bFGF), were originally delineated and have been the subject of extensive research. See, for example, Thomas, *FASEB* 434-40 (1987); Gospodarowicz et al., *J. Cell. Phys. Supp.* 5:15-26 (1987) and PCT publication WO 87/01728, published Mar. 26, 1987. Recently five additional putative members have been identified: FGF-5, see Zhan et al., *Mol. and Cell. Biol.* 8(8):3487-95(1988); FGF.6., see Marics, *Oncogene* 4:335-40(1989); Int-2, see Moore et al., *EMBO J.* 5(5):919-24(1986) and Dickson et al., *Nature* 26:833(1987); KGF; see Finch et al., *Science* 245:752-55(1989); and K-FGF see Delli Bovi et al., *Cell* 50:729-37(1987) and Taira et al., *Proc. Natl. Acad. Sci. USA* 84:2980-84(1987).

INVENTION SUMMARY

K-FGF in particular is a desirable therapeutic agent, useful in the promotion of cell growth and differentiation such as in effecting accelerated healing of wounds, burn tissue, or other damage to mammalian tissues.

The complete sequence for K-FGF derived from an oncogene isolated from Kaposi's sarcoma DNA has been determined. Delli Bovi, *Cell, supra*. However, for use as a therapeutic agent, homogeneous preparations of the protein must be employed. This invention provides such preparations.

In one aspect, the invention provides homogeneous K-FGF, preferably non-glycosylated, and substantially free from association with other non-K-FGF proteins, especially of mammalian origin. The homogeneous K-FGF of this invention, non-glycosylated, is characterized by having a molecular weight of about 21 kD when analyzed by SDS polyacrylamide gel electrophoresis under reducing conditions and moving as a single peak on reverse phase high performance liquid chromatography or appearing as a single band by SDS-PAGE on Coomassie Blue staining. Glycosylated, the homogeneous protein can be characterized by the same parameters, except that it will have a molecular weight of about 24 kD.

In another aspect, the invention provides a process for producing homogeneous K-FGF. The process includes culturing a suitable cell, preferably bacterial, transformed with a cDNA sequence encoding a protein characterized by containing a peptide sequence substantially the same as that of K-FGF. The cDNA sequence employed in this process is also in operative association with a suitable expression control sequence. The K-FGF so produced is then separately recovered in homogeneous, pure form.

In yet another aspect, the invention provides pharmaceutical compositions for use in wound healing comprising effective amounts of the homogeneous K-FGF of this invention in a pharmaceutically acceptable vehicle.

As still another aspect, the invention includes methods of treating mammals having bone or soft tissue wounds comprising administering a therapeutically effective amount of the homogeneous K-FGF of the present invention to the mammal, either alone or in conjunction with a colony stimulating factor such as macrophage colony stimulating factor (M-CSF) or with an osteogenic inducing factor such as bone morphogenic protein (BMP).

DETAILED DESCRIPTION

Figure 1:
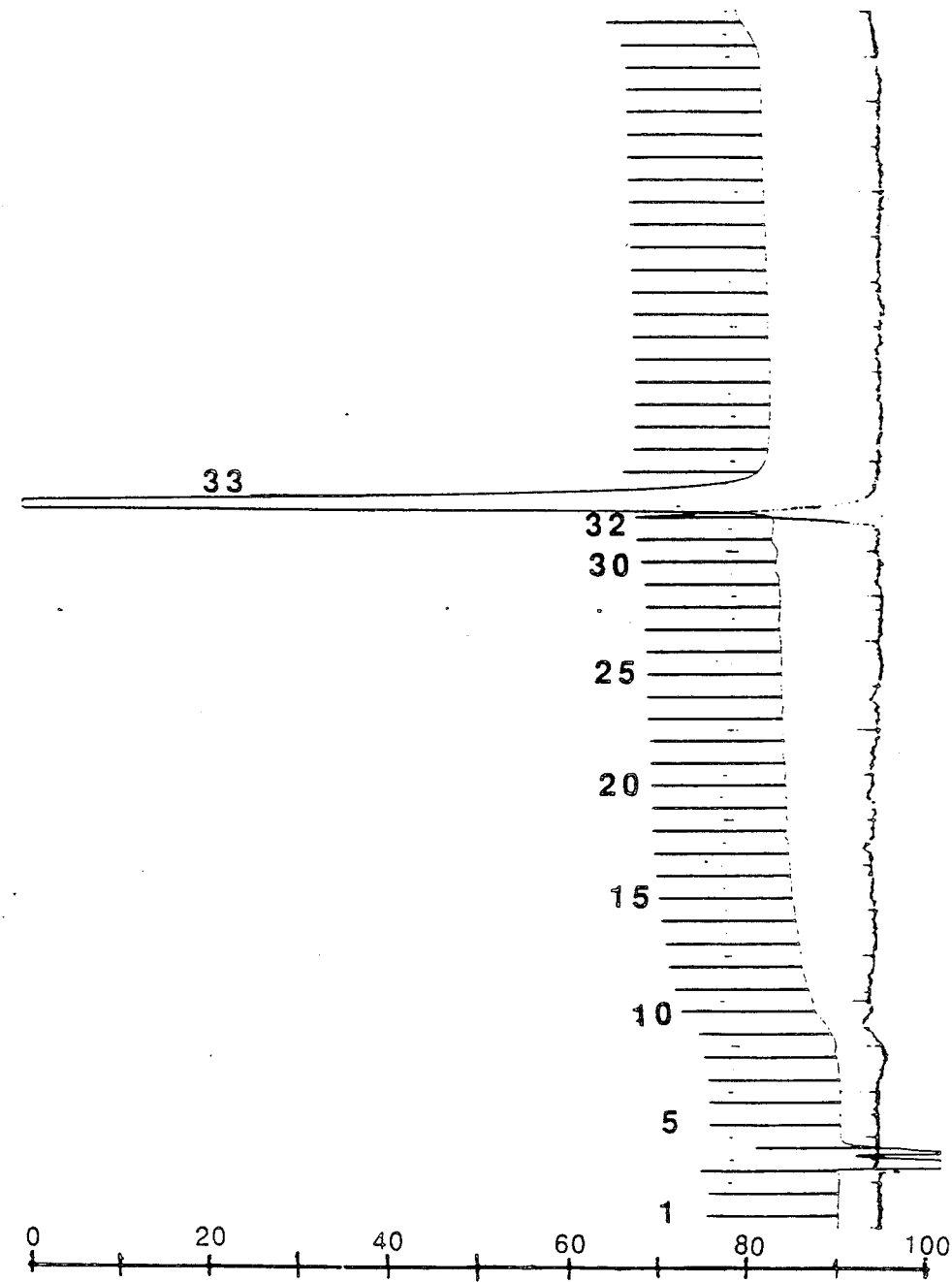
FIG. 1 is a chromatograph showing the elution profile of the homogeneous K-FGF protein of the present invention treated by reverse phase high performance liquid chromatography and illustrating absorbance of fractions at 280 nanometers versus time.

The present invention provides homogeneous K-FGF protein. By "homogeneous", we mean free or substantially free from substances normally accompanying K-FGF in its native state (i.e., as it occurs in nature or in a recombinant cell line), especially from other mammalian proteins. We note that homogeneous K-FGF protein, whether isolated from nature or recombinantly produced in mammalian or in non-mammalian cells, has not to our knowledge ever been reported in the scientific literature heretofore.

In its non-glycosylated form, the homogeneous K-FGF is further characterized by an absence of oligosaccharide moieties attached to the polypeptide chain or portion of the molecule, a molecular weight of about 21,000 daltons by SDS polyacrylamide gel electrophoresis, movement as a single peak on reverse phase HPLC, and appearance as a single band on SDS-PAGE by Coomassie Blue staining. Homogeneous non-glycosylated K-FGF also appears as a single band on reducing SDS-PAGE and has an endotoxin content of less than about 0.125 units per 500 micrograms K-FGF, as assayed by the Limulus Amebocyte Lysate assay [Associates of Cape Cod, Inc.]. It can be additionally characterized by having a half maximal level of $^3$H-thymidine incorporation in the range of about 0.1 to about 1.0 nanograms per milliliter, preferably about 0.4 to about 0.6 nanograms per milliliter and most preferably about 0.5 nanograms per milliliter, in the $^3$H-thymidine uptake assay using Balb C-3T3 cells. Homogeneous glycosylated K-FGF is similar or identical in the foregoing respects except for having a somewhat higher apparent molecular weight by SDS-PAGE, of about 24,000 daltons, due to the presence of attached oligosaccharides. Homogeneous K-FGF may comprise K-FGF having the alanine N-terminus or the proline N-terminus (see Example 1). In either case, all or a portion of the bacterially expressed product may contain the initiator methionine residue. If desired, the initiator methionine residue may be deleted by expressing the K-FGF in a bacterial strain over-expressing the methionine amino peptidase which efficiently removes the terminal methionine.

The present invention also provides a method for producing homogeneous K-FGF, preferably in nonglycosylated form. The method involves culturing a host cell, preferably bacterial, transformed with, i.e., containing and capable of expressing, a DNA sequence encoding the K-FGF protein, which is under the expression control of suitable transcriptional control sequences. The DNA sequence encodes the same mature peptide sequence, or substantially the same mature peptide sequence disclosed in Delli Bovi, Cell 50:729–37(1987), Yoshida, Proc. Natl. Acad. Sci. USA 84:7305–09(1987) and Taira, Proc. Natl. Acad. Sci. USA 84:2980–84(1987), but may be deliberately designed to include preferred codons for expression in bacterial cells as shown in Table 1. In the latter case, the resulting expression product of such deliberately designed DNA sequence may contain the entire mature peptide sequence shown in Table 1 and may also contain a truncated, biologically active, mature peptide sequence beginning with the serine at position 24, counting from the N-terminal alanine.

The DNA encoding human K-FGF can be isolated and cloned using appropriate vectors, selectable markers and recombinant DNA techniques known in the art in accordance with the method of Delli Bovi, Cell 50:729–37(1987); Mol. and Cell. Biol. 8(7):2933–41(1987); Proc. Natl. Acad. Sci. USA 84:5660–64 (1987) or Yoshida, Proc. Natl. Acad. Sci. USA 84:7305–09 (1987) and Taira, Proc. Natl. Acad. Sci. USA 84:2980–84(1987).

A cDNA encoding K-FGF can be obtained by such methods. Genomic DNA encoding K-FGF may also be obtained from a genomic library using a cDNA probe or oligonucleotide probes. Alternatively, a K-FGF-encoding DNA sequence may be prepared synthetically—in whole or in part. The use of intronless, e.g., cDNA, sequences are preferred, since bacterial expression requires intronless sequences. The sequence may also be modified appropriately as shown in Table 1 for expression in bacteria.

The DNA sequence encoding K-FGF may be inserted by conventional methods into an expression vector suitable for the desired host cell as is well known in the art. For bacterial or yeast production, the DNA sequence should not contain introns and preferably, for bacterial, should not encode a secretory leader sequence. For higher eukaryotic expression, it is not necessary to avoid introns or a leader (preferably for eukaryotic expression, the DNA sequence should contain a secretory leader sequence). In any event, the vectors should contain typical vector elements well known in the art including replication sites, selectable markers and transcriptional control sequences compatible with the chosen host. Various strains of E. coli useful as host cells for the production of non-glycosylated, homogeneous K-FGF are also well-known in the art. A nonexclusive list of such strains includes MC1061, DH1, RR1, C600hfl, K803, JA221, HB101, JM101 and various K12 strains including the strain used in the Examples. Alternatively, other bacterial species may be used. Other suitable bacteria include B. subtilis, various strains of Psuedomonas, other bacilli and the like.

K-FGF may also be produced by heterologous expression of a K-FGF encoding sequence in mammalian cells. K-FGF is thus obtainable in glycosylated form, that is, unless glycosylation is prevented. Where desired, glycosylation can be inhibited by tunicamycin or by site-directed mutagenesis of glycosylation sites, as is well known in the art. Suitable mammalian expression vectors and host cells for production of K-FGF are also well known in the art and include, without limitation, the vectors pXM and pMT2 and Chinese hamster ovary (CHO) cells, monkey COS-1 cells and CV-1, HeLa, mouse L-929 and 3T3 cells. The construction and use of some exemplary mammalian vectors and cell lines is discussed in detail in WO 88/00598.

Many strains of yeast cells known to those skilled in the art are also available as host cells for expression of the K-FGF of the present invention. Additionally, where desired, insect cells may be used as host cells. See, for example, Miller el al., Genetic Engineering 8:277–98(Plenum Press 1986) and references cited therein.

When the K-FGF of this invention is expressed in bacterial cells, as is preferred, it may be expressed intracellularly usually without regard to refolding since that is typically unnecessary to obtain the protein in active form, or it may be secreted from bacterial cells in active form, if a secretory leader is retained. Where necessary or desired, as when reduced bioactivity is observed, the K-FGF product may be refolded by purely conventional methods.

In a preferred approach, E. coli cells, genetically engineered to express a K-FGF DNA sequence as described herein, are cultured under suitable conditions permitting the production and intracellular accumulation of K-FGF protein. The cells are then harvested, i.e., separated from the medium in which they were cultured and from any other materials, and lysed and the desired biologically active K-FGF protein is purified from the lysate. The term "biologically active" means a preparation of K-FGF that exhibits a detectable level of mitogenic activity on Balb C-3T3 cells in a $^3$H-thymidine uptake assay. Various purification techniques, such as column chromatography, gel filtration and reverse phase HPLC, might be useful in purifying the desired protein, at least in part. See, for example, Gospodarowicz et al., J. Cell, Phys 122:323–32(1985), Iwane et al., Biochem. and Biophys. Res. Comm. 146:470–77(1987), Fox et al., J. Biol. Chem. 263:18452–58(1988). EP 0 259 953 published Jun. 4, 1987, and EP 0 237 966 published Sep. 23, 1987. We have, however, developed a particularly effective purification method that does not result in a concommitant loss of significant levels of the protein's biological activity.

The preferred purification method, as it applies to bacterially produced K-FGF, comprises contacting the lysate containing the K-FGF with an aqueous solution having a salt concentration greater than about 0.5 M, but less than about 2 M, and permitting the K-FGF to solubilize. Any insoluble material is then removed from the resultant solution, for example by centrifugation or filtration, and the salt concentration of that solution is reduced to effect precipitation of the K-FGF, for example by dialysis or diafiltration. The precipitated K-FGF is then separately recovered from the materials still dissolved, for instance by centrifugation of the mixture and removal of the pellet from the supernatant, or by any other conventional separation methods, including gel filtration or ion exchange chromatography. The recovered K-FGF, which will be about 50% pure, can be further purified by Heparin-Sepharose column chromatography, gel filtration, ion exchange chromatography or various combinations of those or other conventional procedures. The preferred method, which takes advantage of K-FGF's solubility characteristics, results in more efficient and less costly purification as repetitive filtration or chromatographic steps may be eliminated, and avoids the reduction in biological activity that can result from purification by reverse phase HPLC.

In the performance of the preferred method of purification, a variety of neutral salts may be employed. For example, any one of the following may be used: NaCl, KCl, $Na_2SO_4$, $K_2SO_4$, $Na_3C_6H_5O_7$, $NaC_2H_3O_2$, $NH_2SO_4$, with the salt preferably titrated to pH 7.5. NaCl is a preferred salt.

Pharmaceutical compositions containing the homogeneous K-FGF of the present invention may be useful as wound healing or osteogenic inducing agents. Such pharmaceutical compositions may also contain pharmaceutically acceptable carriers, diluents, fillers, salts, buffers, stabilizers and/or other materials well-known in the art. The term "pharmaceutically acceptable" means a material that does not interfere with the effectiveness of the biological activity of the active ingredient(s) and that is not toxic to the host to which it is administered. The characteristics of the carrier or other material will depend on the route of administration.

Administration can be carried out in a variety of conventional ways. Topical administration to the wound or injury site is preferred. In such case, the K-FGF of the present invention will be in the form of a pyrogen-free, topically acceptable liquid or semi-solid formulation such as an ointment, cream, lotion, foam or gel. The preparation of such topically applied formulations is within the skill in the art.

Cutaneous or sub-cutaneous injection may also be employed and in that case the K-FGF of the present invention will be in the form of pyrogen-free, parenterally acceptable aqueous solutions. The preparation of such parenterally acceptable protein solutions, having due regard to pH, isotonicity, stability and the like, is within the skill of the art.

The amount of active ingredient will depend upon the severity of the condition, the route of administration, the mitogenic activity of the homogeneous K-FGF, and ultimately will be decided by the attending physician or veterinarian. It is currently contemplated, however, that the various pharmaceutical compositions should contain about 10 micrograms to about 1 milligram per milliliter of K-FGF.

The homogeneous K-FGF of the present invention can be used for the in vivo treatment of mammals by physicians or veterinarians in a variety of wound or bone related therapeutic applications. Some of these applications include thermal and chemical burns, surgical incisions, decubital ulcers (bed sores), diabetic ulcers, venous statis ulcers, surgical abrasions from plastic surgery or abrasions from other causes, and skin or bone grafts, bone fractures, ligament, cartilage and tendon tears and inflamation of bursas and tendons, although it is anticipated that the homogeneous, preferably non-glycosylated, K-FGF of the present invention would be useful as a pharmacological agent in any soft tissue or musculo-skeletal injury setting. K-FGF may also be used to promote repair of damaged central and peripheral nerve tissue and for those indications may optionally be used in combination with a nerve growth factor. In sum, the method and compositions of the present invention may be used in the treatment of soft tissue injuries characterized by epidermal injury or discontinuity or by blood vessel disruption and in the treatment of musculo-skeletal and nerve tissue disorders and injuries.

In practicing the method of treatment of this invention, a therapeutically effective amount of K-FGF is administered to a mammal having such an injury or wound. The term "therapeutically effective amount" means the total amount of each active component of the method or composition that is sufficient to show a meaningful patient benefit, i.e., healing of chronic conditions or increase in rate of healing. When applied to an individual active ingredient, administered alone, the term refers to that ingredient alone. When applied to a combination, the term refers to combined amounts of the active ingredients that result in the therapeutic effect, whether administered in combination, serially or simultaneously. A therapeutically effective dose of the K-FGF of this invention is contemplated to be in the range of about 10 micrograms to about 1 milligram per milliliter per application. The number of applications may vary, depending on the individual patient and the severity of the injury. For topical administration, standard topical formulations can be employed.

The homogeneous K-FGF of the present invention may be administered alone or combined with other therapies. For example, the K-FGF may be efficaciously combined with a colony stimulating factor that will function as a chemotatic agent, promoting cell migration into the injured area and stimulating cell growth. A preferred colony stimulating factor is M-CSF. It is contemplated that the administration of M-CSF will serve to debride the wound or burn and speed clearing, thereby permitting the homogeneous K-FGF to promote healing more quickly.

Figure 2:
FIG. 2 is a SDS-PAGE gel profile of the homogeneous K-FGF protein of the present invention treated in accordance with Example 3 and illustrating a single component having an approximate apparent molecular weight of 21 kD.

Various forms or species of M-CSF have been isolated and produced by purification from natural sources or by recombinant DNA techniques. See, for example, Wong et al., Science 235:1504–08(1987), W087/06954, EP 0 261 592, W088/03173, EP 0276 551, U.S. Ser. No. 4,847,201, EP 0249 477, GB 2 016 777, W089/03881, U.S. Ser. No. 4,847,325, W088/08003 and W086/04587. It is contemplated that any M-CSF, including but not limited to those set forth in the publications just cited, may be employed in the method of this invention, as long as that M-CSF exhibits its characteristic biological activity, the ability to proliferate the growth of cells predominantly of the monocyte/macrophage lineage in the standard bone marrow assay of Wong et al., *Science* 235:1504–08(1987), and are encoded by DNAs capable of hybridizing, especially under stringent conditions, to DNAs for the naturally occurring form, as shown in FIG. 2 of Wong, supra. Also included, of course, are naturally-occurring isotypes or allelic variations in the proteins or in their coding sequences, as occur in different members of a species.

A pharmaceutical composition containing a species of M-CSF as the active ingredient may be administered parenterally, e.g. intravenously or subcutaneously. When administered parenterally, the M-CSF composition may be in the form of a non-pyrogenic, sterile, parenterally acceptable aqueous solution. The preparation of such solutions is within the level of skill in the art.

When employed in combination with the homogeneous K-FGF of the present invention, the M-CSF pharmaceutical composition may be administered with the K-FGF composition, preferably prior to or simultaneously therewith. In any case, a therapeutically effective dose is contemplated to be in the range of about 10–200 micrograms M-CSF/kg/day, preferably in the range of about 20–100 micrograms/kg/day.

K-FGF may also be efficaciously combined with an osteogenic inducing factor such as BMP that will function as a bone or cartilage growth mediating agent. It is contemplated that administration of BMP in combination with the K-FGF of the present invention will additively or synergistically increase the rate of formation of cartilage and bone, thereby speeding recovery from cartilage and bone injuries, joint replacement surgeries, plastic surgery, chronic bone disorders, periodontal disease and the like.

Various forms or species of BMP have been isolated and produced. See, for example, WO 88/00205 and PCT Application No. U.S. Pat. No. 89/01464 filed Apr. 7, 1989. It is contemplated that any BMP, including but not limited to those set forth in the publications just cited, may be employed in the method of this invention, as long as that BMP exhibits its characteristic biological activity, the ability to induce cartilage and/or bone formation in the Rosen-modified Sampath-Reddi rat bone formation assay described in the foregoing publications (see also, Sampath and Reddi, *Proc. Natl. Acad. Sci. USA* 80:6591–95(1983)), and are encoded by DNAs capable of hybridizing, especially under stringent conditions, to DNAs disclosed therein. Also included, of course, are naturally-occuring isotypes or allelic variations in the proteins or in their coding sequences, as occur in different members of a species. A preferred form is BMP-2.

A pharmaceutical composition containing a species of BMP as the active ingredient may be administered topically, systematically, or locally as an implant or device. When administered, the BMP composition may be in a pyrogen-free, physiologically acceptable form and may be encapsulated or injected in a viscous form for delivery to the site of bone or cartilage damage, or may include a matrix capable of delivering the BMP to the site of damage and providing a surface and support structure for the developing bone or cartilage. Such matrices, optimally capable of being resorbed into the body, may be formed of materials currently in use for other medical implant applications and are known in the art.

When employed in combination with the homogeneous K-FGF of the present invention, the BMP pharmaceutical composition may be administered either before, after or simultaneously with the K-FGF. In any case, a therapeutically effective dose is contemplated to be in the range of about 10 to about $10^6$ nanograms of BMP per gram of bone weight desired.

It is also contemplated that other members of the FGF family might be efficaciously combined with the foregoing colony stimulating factors or osteogenic inducing factors in treating the indications discussed.

The invention is further described in the following examples, which are intended to illustrate the invention without limiting its scope.

EXAMPLE 1 cDNA Subcloning and *E Coli* Expression

While a variety of different vector types and expression systems may be used, we designed and constructed the bacterial expression vector, pAYLC/KSF(A)-781, which contains a K-FGF encoding intronless cDNA sequence under the expression control of the pL promoter and a cII ribosome binding site. The cDNA coding sequence was modified to contain a MET codon in place of the native secretory leader sequence and the non-coding sequence at the 3' end was truncated, as shown in Table 1. In addition, 32 of the first 33 codons of the sequence were modified to reduce the G/C content, from 76% in the native sequence to 48% in the modified sequence. The individual nucleotide substitutions are shown, as inserted in each codon; the native nucleotides replaced are shown above the codons. For mammalian expression, the native secretory sequence, the complete 3'non-coding sequence and the native codons may be used. See Delli Bovi, *Cell, supra*

TABLE 1

| | | | | | | | | | | | | | | | (ATG) (MET) | A GCT* Ala* |
|---|---|---|---|---|---|---|---|---|---|---|---|---|---|---|---|---|
| C | T | A | C | C | C | G | G | G | C | G | G | G | C | C | | |
| CCA Pro | ACA Thr | GCT Ala | CCA Pro | AAT Asn | GGT Gly | ACT Thr | CTA Leu | GAA Glu | GCT Ala | GAA Glu | CTA Leu | GAA Glu | CGT Arg | CGT Arg | TGG Trp | |
| G | AGC | G | G | G | C | G | T G | G | C | G | G | G | A | G | G | |
| GAA Glu | TCT Ser | CTA Leu | GTT Val | GCT Ala | CTA Leu | TCT Ser | CTA Leu | GCT Ala | CGT Arg | CTA Leu | CCA Pro | GTA Val | GCT Ala | GCT Ala | CAA Gln | |
| CCC Pro | AAG Lys | GAG Glu | GCG Ala | GCC Ala | GTC Val | CAG Gln | AGC Ser | GGC Gly | GCC Ala | GGC Gly | GAC Asp | TAC Tyr | CTG Leu | CTG Leu | GGC Gly | |
| ATC Ile | AAG Lys | CGG Arg | CTG Leu | CGG Arg | CGG Arg | CTC Leu | TAC Tyr | TGC Cys | AAC Asn | GTG Val | GGC Gly | ATC Ile | GGC Gly | TTC Phe | CAC His | |
| CTC Leu | CAG Gln | GCG Ala | CTC Leu | CCC Pro | GAC Asp | GGC Gly | CGC Arg | ATC Ile | GGC Gly | GGC Gly | GCG Ala | CAC His | GCG Ala | GAC Asp | ACC Thr | |
| CGC Arg | GAC Asp | AGC Ser | CTG Leu | CTG Leu | GAG Glu | CTC Leu | TCG Ser | CCC Pro | GTG Val | GAG Glu | CGG Arg | GGC Gly | GTG Val | GTG Val | AGC Ser | |

TABLE 1-continued

| ATC | TTC | GGC | GTG | GCC | AGC | CGG | TTC | TTC | GTG | GCC | ATG | AGC | AGC | AAG | GGC |
|-----|-----|-----|-----|-----|-----|-----|-----|-----|-----|-----|-----|-----|-----|-----|-----|
| Ile | Phe | Gly | Val | Ala | Ser | Arg | Phe | Phe | Val | Ala | Met | Ser | Ser | Lys | Gly |
| AAG | CTC | TAT | GGC | TCG | CCC | TTC | TTC | ACC | GAT | GAG | TGC | ACG | TTC | AAG | GAG |
| Lys | Leu | Tyr | Gly | Ser | Pro | Phe | Phe | Thr | Asp | Glu | Cys | Thr | Phe | Lys | Glu |
| ATT | CTC | CTT | CCC | AAC | AAC | TAC | AAC | GCC | TAC | GAG | TCC | TAC | AAG | TAC | CCC |
| Ile | Leu | Leu | Pro | Asn | Asn | Tyr | Asn | Ala | Tyr | Glu | Ser | Tyr | Lys | Tyr | Pro |
| GGC | ATG | TTC | ATC | GCC | CTG | AGC | AAG | AAT | GGG | AAG | ACC | AAG | AAG | GGG | AAC |
| Gly | Met | Phe | Ile | Ala | Leu | Ser | Lys | Asn | Gly | Lys | Thr | Lys | Lys | Gly | Asn |
| CGA | GTG | TCG | CCC | ACC | ATC | AAG | GTC | ACC | CAC | TTC | CTC | CCC | AGG | CTG | TGA |
| Arg | Val | Ser | Pro | Thr | Met | Lys | Val | Thr | His | Phe | Leu | Pro | Arg | Leu | --- |
| CCC | TCC | AGA | GGA | CCC | TTG | CCT | CAG | CCT | CGG | GAA | GCC | CCT | GGG | AGG | GCA |
| GTG | CGA | GGG | TCA | CCT | TG  |     |     |     |     |     |     |     |     |     |     |

A second expression vector, pAYLC/KSF(P)-781, was also constructed. This vector differs from the parent vector by the deletion of the first mature codon (Ala*) from the K-FGF coding region, leaving a proline codon as the first codon after the initiator methionine codon. See Table 1.

The bacterial host cell used was GI 595, a genetically engineered strain of *E. coli* strain W3110, which is reliant on pAYLC/KSF(A)-781 or pAYLC/KSF(P)-781 for growth in media unsupplemented with thymine or thymidine.

Expression of K-FGF from strain GI 595, using vector pAYLC/KSF(A)-781, was accomplished by growing the cells in media lacking thymine or thymidine to mid-logarithmic phase at 30 degrees C. At this temperature the cI857 lambda repressor effectively suppresses transcription from the pL promoter. The culture was then shifted to 40 degrees C. to induce transcription of the K-FGF gene from pL. The nonglycosylated K-FGF product was allowed to accumulate by maintaining incubation at 40 degrees C. before harvest. The cells were harvested and stored at −80 degrees C.

Expression of K-FGF using vector pAYLC/KSF(P)-781 can be accomplished in the same manner.

EXAMPLE 2

Purification 100 grams of the frozen *E. coli* cell material harvested and stored as in Example 1 above was combined with 0.5 L of Break Buffer (6.0 g/l Tris, pH adjusted to 7.0 with HCl, 1.9 g/l EDTA, 1.7 g/l PMSF, 1.0 g/l pABA (p-aminobenzamidine) and 50 ml/l glycerol) in a 4 L Waring commercial blender. The frozen cell material was blended for approximately 1 minute at the highest power setting under a nitrogen atmosphere. The cell suspension was transferred to a sample reservoir of a prechilled (at 4 degrees C. for 12 hours) model 15 M Gaulin laboratory homogenizer. The cells were subjected to three passes through the homogenizer, set at a pressure differential of 8000 to 9000 PSI. Cell breakage was monitored visually by 1000 × phase contrast microscopy. Lysed cell material was extruded from the homogenizer after the third pass directly into a 10 L Nalgene cryogenic Dewar filled with liquid nitrogen.

150 grams of this lysed cell material was removed from the Dewar. To this lysate was added 50 ml of 50 mM Hepes, pH 7.5, containing 5 mM pABA, 5 mM EDTA, and 1 mM PMSF, and the mixture was stirred for one hour at 4 degrees C. The suspension was forced through a 23 gauge needle using a 60 ml syringe and centrifuged at 25000×g for 50 minutes at 4 degrees C. The supernatant was discarded. To the pellet was added 150 ml of 50 mM Hepes, 1.0 M NaCl, pH 7.5, containing 5 mM pABA, 5 mM EDTA, and 1 mM PMSF. This was stirred for 15 hours at 4 degrees C. The suspension was then centrifuged at 25000×g for 45 minutes at 4 degrees C. The supernatant was decanted and dialyzed at 4 degrees C. against two 2.0 liter volumes of 50 mM Hepes, pH 7.5. The dialysate was centrifuged at 10000×g for 30 minutes at 4 degrees C. The supernatant was discarded and the pellet was redissolved in 200 ml of 50 mM Hepes, 0.75 M NaCl, pH 7.5, by stirring at 4 degrees C. for 6 hours and then centrifuged at 25000×g for 30 minutes at 4 degrees C. The resulting supernatant solution was diluted by adding 400 ml of 50 mM Hepes, pH 7.5, and passed over a Q Toyo-Pearl column (7.5×2.5 cm) at 1.25 ml/minute that had previously been equilibrated with 50 mM Hepes, 0.25 M NaCl, pH 7.5. The eluate, about 650 ml, was collected and the concentration of NaCl was raised to 0.75M by the addition of solid NaCl. The solution was loaded onto a Heparin-Sepharose column (10.0×1.5 cm) at 4 degrees C. and eluted with a gradient of 0.75 to 1.5 M NaCl in 50 mM Hepes, pH 7.5. The K-FGF eluted at approximately 1.1 M NaCl and was found to be homogeneous by SDS-PAGE/Coomassie Blue staining and further characterization studies.

It is noted that other materials can be substituted for the specific materials enumerated in this Example. For instance, any equilibrated column of strong anionic resin can be substituted for the Q Toyo-Pearl column and any Heparin-based affinity column can be used. Such substitution of materials is within the level of skill in the art.

EXAMPLE 3

Molecular Weight Determination

Protein samples obtained as in Example 2 were analyzed using sodium dodecyl sulfate polyacrylamide gel electrophoresis ("SDS-PAGE") as described by Laemmli. *Nature* 15 *Vol.* 22 (259):680–85(1970). Molecular weight determinations were performed by SDS-PAGE as follows:

Aliquots containing 10 micrograms of protein were added to the sample buffer composed of 125 mM Tris, pH 6.8, 4% sodium dodecyl sulfate, 20% glycerol, 10% 2-mercaptoethanol and 0.05% bromophenol blue. Samples were boiled for 3 minutes and then applied to a 12.5% polyacrylamide gel slab (0.75 mm) with a 4% stacking gel. Electrophoresis under non-reducing conditions was performed in identical fashion, except that the 2-mercaptoethanol was omitted from the buffer and the samples were not boiled. A protein standard mixture containing 10 micrograms per standard was also applied to each gel. SDS-PAGE revealed a single component having an approximate apparent molecular weight of 21 kD.

EXAMPLE 4

Reverse Phase HPLC

Approximately 0.2 ml of the purified material from Example 2 was injected onto a C-4 Vydac R-P HPLC column (25×0.45 cm) and fractionated by reverse phase HPLC using the gradient conditions described in Table 2. A single protein peak, as shown in the figure, was detected by UV absorption at 280 nm. The identity of K-FGF was confirmed by behavior on SDS-PAGE and N-terminal amino acid sequencing.

TABLE 2

| Pump A 0.1% Trifluoroacetic Acid (TFA) in water Pump B 95% Acetonitrile in 0.1% TFA in water | | |
|---|---|---|
| Gradient Time (min) | % B | Duration |
| 0 | 20 | 1 |
| 1 | 30 | 5 |
| 6 | 50 | 40 |
| 46 | 100 | 10 |
| 55 | 0 | 2 |

The homogeneity of the protein was confirmed by this procedure. However, significant loss of biological activity was observed. For best results therefor, the protein can be purified as in Example 2.

EXAMPLE 5

Coomassie Blue Staining

The gel slab from Example 3 was stained with Coomassie Blue R-250 as follows: approximately 250 ml of 0.05% Coomassie Blue R-250 in 25% isopropanol, 10% acetic acid, was heated to 60 degrees C. The gel was soaked in this solution for one hour with gentle rocking. The gel was destained with several 250 ml aliquots of 10% isopropanol, 10% acetic acid, until the background was clear and showed no blue color. A single band was revealed upon destaining.

EXAMPLE 6

$^3$H-Thymidine Uptake Assay

K-FGF obtained as in Example 2 was assayed for its mitogenic effect on Balb C-3T3 cells using a $^3$H-thymidine uptake assay. Cells were grown to near confluence in DME (Dulbecco's modification of Eagle's Medium [Hazelton]), 1 mM glutamine and 10% calf serum [Gibco]in 96 well plates, washed with PBS and starved for 2-3 days in DME, 1 mM glutamine and 0.5% calf serum. K-FGF was added in serial dilutions to the wells in triplicate and the plates incubated for 20 hours before adding 1 microcurie per well of $^3$H-thymidine. After an additional 4 hours, cells were released from the plates by the addition of trypsin to 1%. The cells were transferred to a filter using a 'Cell Harverster' Model 1295-001 [LKB], washed with water, and finally with 70% ethanol. The amount of 3H-thymidine incorporation was measured in a 'Betaplate', Model 1205 scintilation counter [LKB] and the results plotted graphically to determine the concentration of K-FGF that resulted in 50% of the maximum incorporation of $^3$H-thymidine. This was determined to be about 0.5 nanograms of K-FGF per ml in this assay.

EXAMPLE 7

Solubility

The solubility of the nonglycosylated K-FGF, partially purified to about the 50% level using the salt precipitation procedure of Example 2, was compared to the solubility of the homogeneous, nonglycosylated K-FGF of that Example, further purified using Q Toyo-Pearl and Heparin-Sepharose column chromatography to remove protein impurities and pyrogens. Solubility of the partially purified K-FGF was found to be dependent on ionic strength (between 50 and 1000 mM NaCl) and independent of pH (between pH 7.5 and pH 9.0). There was no major improvement in solubility between 0.5 and 1.5 M NaCl. The maximum solubility observed was about 1 mg/ml.

The solubility behavior of the purified, pyrogen-free K-FGF produced as in Example 2 was very different from the partially purified protein. Concentrations of 500–800 micrograms/ml were observed for the purified protein in the absence of any additional salts (50 mM Hepes, pH 7.5).

EXAMPLE 8

Use in Would Healing

The homogeneous, E. coli produced K-FGF of Example 2 was evaluated for use as a wound healing agent using the porcine wound healing model of Winter, *Epidermal Wound Healing*, pps. 71–112 (Maibach, HI and Rovee, DT, eds.), Year Book Medical Publishers, Inc., Chicago, as modified by Eaglstein and Mertz, *J Invest Dermatol* 71:382–84(1978). Five, young white Yorkshire pigs, 20–30 lbs each, and approximately two to three months old were used. The hair on the back and sides of each animal was clipped with standard animal clippers and the exposed skin washed and rinsed with mild soap and water. The pigs were anesthetized with ketamine (300 mg i.m.) and halothane (3%, open mask). Two hundred rectangular 7×10 mm wounds, 0.3 mm deep, were made in the thoracic and lumbar paravertebral areas of each animal with a Castro-Viejo dermatome. The wounds on each animal were divided into five treatment sites forty wounds per treatment site) and each treatment site on each animal was treated with one of the following on day 0:

| | |
|---|---|
| C | air exposed control, no treatment |
| T1 | 10 micrograms K-FGF/20 microliters aqueous vehicle/wound |
| T2 | 1 microgram K-FGF/20 microliters aqueous vehicle/wound |
| T3 | 0.1 microgram K-FGS/20 microliters aqueous vehicle/wound |
| V | aqueous vehicle only, composed of 50 mM Hepes, pH 7.5, and 125 mM NaCl, 20 microliters/wound |

To allow for uniform distribution, the foregoing treatments were applied to each animal at a different treatment site.

The aqueous treatments were topically applied and left undisturbed for 30 minutes to permit complete absorption into the wound bed. Daily, from days 3 through 7, wound samples were taken from five wounds, randomly chosen, in each treatment site on each animal by excision with a Castro-Viejo dermatome (22×33 mm deep including the entire wound bed and some surrounding untreated tissue). The samples were evaluated in accord with the method of Mertz et al., *Swine in Biomedical Research*, pp 291-302, (Tumbleson, Me., ed.), Plenum Press, New York. The homogeneous K-FGF of this invention caused an increase in the relative rate of healing of between about 1o and about 20% over the untreated controls.

We claim:

1. Homogeneous K-FGF polypeptide, further characterized by:
   a molecular weight of about 21,000 daltons when analyzed by SDS polyacrylamide gel electrophoresis under reducing conditions;
   the absence of oligosaccharide moieties attached to the polypeptide;
   movement as a single peak on reverse phase high performance liquid chromatography;
   appearance as a single band on reducing SDS-PAGE; and
   a detectable level of mitogenic activity on Balb C-3T3 cells in a $^3$H-thymidine uptake assay;
wherein said K-FGF is substantially free from other mammalian proteins.

2. A process for purifying bacterially produced K-FGF of claim 1 from a mixture comprising contacting the mixture with an aqueous solution having a salt concentration between about 0.5 and 2.0 M and permitting the K-FGF to solubilize;
   removing any insoluble material from the aqueous solution;
   reducing the salt concentration of the aqueous solution to precipitate the K-FGF; and
   recovering the precipitated K-FGF from the materials still dissolved.

3. A pharmaceutical composition comprising a therapeutically effective amount of the homogeneous K-FGF of claim 1 in a pharmaceutically acceptable vehicle.

4. The pharmaceutical composition of claim 3, for tropical administration wherein the pharmaceutically acceptable vehicle is selected from the group consisting of an ointment, lotion, foam, and a gel.

5. The pharmaceutical composition of claim 4, wherein the pharmaceutically acceptable vehicle is an ointment.

6. The pharmaceutical composition of claim 4, wherein the pharmaceutically acceptable vehicle is a lotion.

7. The pharmaceutical composition of claim 4, wherein the pharmaceutically acceptable vehicle is a foam.

8. The pharmaceutical composition of claim 4, wherein the pharmaceutically acceptable vehicle is a gel.

* * * * *